United States Patent
Hahn et al.

[11] Patent Number: 5,453,507
[45] Date of Patent: Sep. 26, 1995

[54] PROCESS FOR PREPARING 4-ISOTHIAZOLIN-3-ONE

[75] Inventors: Soon Jang Hahn, Seoul; Jin Man Kim; Young Park, both of Kyungki, all of Rep. of Korea

[73] Assignee: Sunkyong Industries Co., Ltd., Rep. of Korea

[21] Appl. No.: 146,172

[22] PCT Filed: May 11, 1992

[86] PCT No.: PCT/KR92/00014

§ 371 Date: Feb. 4, 1994

§ 102(e) Date: Feb. 4, 1994

[87] PCT Pub. No.: WO92/20664

PCT Pub. Date: Nov. 26, 1992

[30] Foreign Application Priority Data

May 10, 1991 [KR] Rep. of Korea .............. 91-7541
Nov. 7, 1991 [KR] Rep. of Korea .............. 91-19719
Nov. 18, 1991 [KR] Rep. of Korea .............. 91-20482

[51] Int. Cl.⁶ ............................ C07D 275/03
[52] U.S. Cl. ............................ 548/213
[58] Field of Search ..................... 548/213

[56] References Cited

U.S. PATENT DOCUMENTS

5,312,827  5/1994  Bayer ........................ 548/213

FOREIGN PATENT DOCUMENTS

0095907  12/1983  European Pat. Off. .

OTHER PUBLICATIONS

Lewis, J. Het. Chem 8, 571 (1971).

Miller et al., "Isothiazoles II: 5-Chloro-4-isothiazolin-3-ones," Research Division, Rohm and Haas Company, Spring House, Pa. Aug. 1971, vol. 8, pp. 581–586.

*Primary Examiner*—Robert Gerstl
*Attorney, Agent, or Firm*—Kenyon & Kenyon

[57] ABSTRACT

The present invention relates to an improved process for selectively preparing 4-isothiazolin-3-one having the following structural formula(I), consisted of preparing 3,3'-dithiodipropionyldichloride by reacting 3,3'-dithiodipropionic acid with thionylchloride, reacting with amine compound to prepare 3,3'-dithiodipropioneamide, and herein adding sulfrylchloride in organic solvent to cyclize, which is useful as antiseptic or anti-infectives for cooling water, metal processing oils, paints, cosmetics, surfactants, sensitizers, etc.

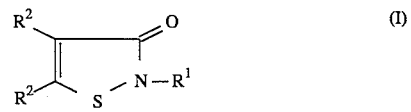

wherein,
$R^1$ is methyl or n-octyl group;
$R^2$ is hydrogen or chlorine atom.

4 Claims, No Drawings

5,453,507

1
PROCESS FOR PREPARING 4-ISOTHIAZOLIN-3-ONE

This Application is a 371 of PCT/KR 92/00014 filed May 11, 1992.

BACKGROUND OF THE INVENTION

Field of the Invention

The present invention relates to a process for preparing 4-isothiazolin-3-one, in particular to improved method for selectively preparing 4-isothiazolin-3-one having the following structural formula(I) which is useful as an antiseptic or anti-infectives in the field of cooling waters or metal processing oils for industrial, paints, cosmetics, sufactants, sensitizers. etc.

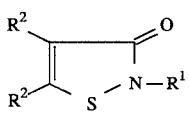

wherein.

$R^1$ is methyl or n-octyl group:
$R^2$ is hydrogen or chlorine atom.

European Patent Publication No. 0095907 discloses a method for manufacturing 4-isothiazolin-3-one derivatives as a mixture of two substance by carring out amidation reaction in accordance with the following scheme(A) and cyclization reaction of the following scheme(B).

[Scheme(A)]

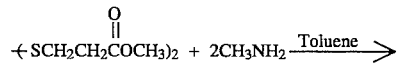

$+SCH_2CH_2CNHCH_3)_2$

[Scheme(B)]

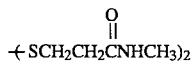

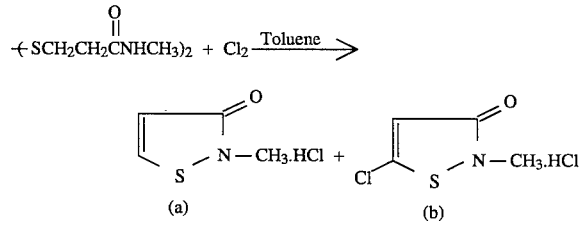

Also, Journal of Heterocyclic Chemistry, 1971, 8 discloses a synthetic method of 2-t-octyl-4-isothiazolin-3-one having structure being similar to the above formula(I), by carting out amidation reaction in accordance with the following scheme(C) and chlorization and cyclization according to the following scheme(D).

[Scheme(C)]

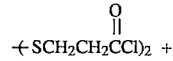

2

-continued
[Scheme(C)]

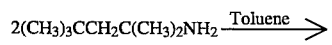

[Scheme(D)]

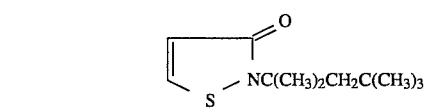

But, according to the method of European Patent Publication No. 0095907, mixture of two substance, 2-methyl-4-isothiazolin-3-one of the above formula(a) and 5-chloro-2-methyl-4-isothiazolin-3-one of the above formula(b), is manufactured as a necessary, and then 5-chloro-2-methyl-4-isothisolin-3-one of the formula(b) has higher virulence than the formula(a).

Therefore, the product mixed cannot be used for the human body, and cannot be used for a long time because of being stability at room temperature and so used within the limits. Also, the yield is low.

Nevertheless, a method for selectively preparing or separating the formula(a) has not been developed, and if it may be separated, the process is intricate and uneconomical. So, the mixed product has been used as it is.

The method disclosed in Journal of Heterocyclic Chemistry is to prepare 2-t-octyl-4-isothiazolin-3-one by using $Cl_2$ gas and toluene as solvent on the scheme(D), but the product is not the compound of structure having n-octyl group.

SUMMARY OF THE INVENTION

The object of the present invention is to provide a new process for selectively preparing the compound of the above formula(I) to high yield.

The present invention relates to a process for selectively preparing 4-isothiazolin-3-one having the above sturctural formula(I) characterized in which consists of preparing 3,3'-dithiodipropionyldichloride of following formula(II), by reacting 3,3'-dithiodipropionic acid with thionylchloride, reacting with amine compound to prepare 3,3'-dithiodipropionamide derivative of following formula(III) and herein adding sulfurylchloride of following formula(IV) in organic solvent to cyclize.

  (II)

  (III)

  (IV)

wherein,
$R^1$ is as defined in the above formula(I)

X is halogen atom.

DETAILED DESCRIPTION OF THE INVENTION

The present invention relates to the process for selectively preparing 4-isothiazolin-3-one of the above formula(I) by using 3,3'-dithiodipropionic acid, thionylchloride, amine compound and sulfurylchloride of the above formula(IV), and then 3,3'-dithiodipropionic acid is reacted with thionyl chloride to ratio of 1:2 to 1:4 by mole at 10°~30° C. to obtain 3,3'-dithiodipropionyl dichloride of the above formula(II). If the reacting mole ratio of thionylchloride is less than 1:2, the unreacted impurity may be occured, and if excess of 1:4, it is uneconomical as unnecessary on the chemical reaction.

Also, if the reacting temperature is lower than 10° C., the reation time is very long, and if over 30° C., it is dangerous to operate because of generation of toxic thionylchloride vapor.

The compound of formula(II) is reacted with amine compound selected from methyl amine or n-octylamine to 1:2 to 1:6 by mole at −10° C.~35° C., preferably −10° C.~30° C., more preferably 15° C. to room temperature.

If the reacting temperature is lower than −10° C., it is uneconomical, and if over 35° C., it is dangerous of explosion due to an exothermic reaction. Also, if the reacting mole ratio of amine compound is less than 1:2, the unreacted impurity may be occured, and if excess of 1:6, it is uneconomical as unnecessary on the chemical reaction. In this reaction, toluene or benezene may be used as reaction solvent.

The obtained 3,3'-dithiodipropionamide derivative of the above formula(III) according to the above process is cyclized in organic solvent by adding sulfurylchloride of the above formula(IV) to selectively afford the desired compound of formula(I). In case of $R^2$=H in the formula(I), the compound of formula(III) is reacted with sulfurylchloride to 1:1 to 1:5 by mole, preferably 1:2 to 1:3. If the reacting mole ratio of sulfurychloride is less than 1:1, the unreacted impurity may be occured, and if excess of 1:5, the purity and economicity is reduced by side reaction.

Meanwhile, in case of $R^2$=Cl in the formula(I), the using mole ratio of the compounds may be a range of 1:5 to 1:25 by mole ratio, and then the reaction may be carried out at 50° C. and below, preferably −20° C.~50° C. If the reaction temperature is higher than 50° C., the yield may be remarkably reduced by deterioration of stability for the final product. In this reaction, organic solvent, i.e. organic halogen compounds such as $CH_2X_2$, $CHX_3$, $CX_3CH_3$, $CHX_2CHX_2$, etc. (wherein, X is halogen), may be used as reaction solvent.

4-Isothizolin-3-one compound of the above formula(I) prepared to the process according to the present invention is selectively obtained as the pure compound without impurities, and then the yield is more than 90%.

The compound of formula(I) is a stable and durable biocide, and may be used for anti-algoid agents on cooling tower, antiseptics for paint, metal processing, cosmetic, shampoo, paper or surfactant, antimold or anti-infectives.

According to the present invention,4-isothiazolin-3-one is selectively prepared only without production of 5-chloro-2-methyl-4-isothiazolin-3-one or 4,4,5,5-tetrachloro-2-n-octyl-4-isothiazolin-3-one, as impurity, which is corrosive substance under atmosphere and is resoluted under atmosphere within few weeks due to reduction of stability.

Therefore, the compound of the present invention is useful for various field as the above. In particular, since the toxicity is remarkably low, it may be used for cosmetics or shampoo to directly apply in human body, and this compound may be used to maintain the primary effect for a long time.

Also, the process according to the present invention is simple and econonical method compared to prior art, and has an advantage to prepare the desired product to high yield.

EXAMPLE 1

A thermometer and dropping funnel were equiped with 1 l three-necked flask, and N,N dimethyl 3,3'-dithiodipropionamide (23.6 g, 0.1 mol) was dissolved in 350 ml of methylenechloride in the flask. The solution was maintained below 5° C. in cryostat, and herein sulfurylchloride (40.5 g, 0.3 mol) was added dropwise and simultaneously stirred for 3 hr.

After stirring at 0° C. for 1 hr, the temperature was slowly increased to room temperature and maintained at 25°±5° C. in water bath, and then the solution was stirred for 3 hr.

The obtained white precipitate was filtered by suction, and then the remaining methylenechloride was removed at 50° C. for 3 hr in vacuum oven to obtain 2-methyl-4-isothiazolin-3-one.HCl (27.0 g, 90 mol %).

$^1$H-NMR (100 MHz, $D_2O$):δ ppm; 8.52(d, 5H), 6.35(d, 4H), 3.41(s, $CH_3$)

EXAMPLE 2

A thermometer and dropping funnel were equiped with 1 l three-necked flask, and 3,3'-dithiodipropionamide (23.6 g, 0.1 mol) was dissolved in 350 ml of methylenechloride in the flask. The solution was maintained below 5° C. in cryostat, and herein sulfurylchloride (33.75 g, 0.25 mol) was added dropwise and simultaneously stirred for 3 hr.

After stirring at 0° C. for 1 hr, the temperature was slowly increased to room temperature and maintained at 30°±5° C. in water bath, and then the solution was stirred for 3 hr.

The obtained white precipitate was filtered by suction, and then the remaining methylenechloride was removed at 50° C. for 3 hr in vacuum oven to obtain 2-methyl-4-isothiazolin-3-one.HCl (27.4 g, 90 mol %).

$^1$H-NMR(100 MHz, $D_2O$):δ ppm; 8.53(d, 5H), 6.34(d, 4H), 3.41(s, $CH_3$)

EXAMPLE 3

A thermometer and dropping funnel were equiped with 1 l three-necked flask, and N,N dimethyl 3,3'-dithiodipropionamide (23.6 g, 0.1 mol) was dissolved in 350 ml of methylenechloride in the flask. The solution was maintained below −5° C. in cryostat, and herein sulfurylchloride (28.35 g, 0.21 mol) was added dropwise and simultaneously stirred for 3 hr.

After stirring at −5° C. for 1 hr, the temperature was slowly increased to room temperature and maintained at 35° C. in water bath, and then the solution was stirred for 3 hr.

The obtained white precipitate was filtered by suction, and then the remaining methylenechloride was removed at 50° C. for 3 hr in vacuum oven to obtain 2-methyl-4-isothiazolin-3-one.HCl (27.8 g, 91.7 mol %).

$^1$H-NMR(100 MHz, $D_2O$):δ ppm; 8.53(d, 5H), 6.33(d, 4H), 3.41(s, $CH_3$)

EXAMPLE 4

A thermometer and dropping funnel were equiped with 1 l three-necked flask, and 3,3'-dithiodipropionamide (23.6 g, 0.1 mol) was dissolved in 350 ml of methylenechloride in the flask. The solution was maintained below −5° C. in cryostat, and herein sulfurylchloride (40.5 g, 0.3 mol) was added dropwise and simultaneously stirred for 3 hr.

After stirring at 0° C. for 1 hr, the temperature was slowly increased to room temperature and maintained at 40° C. in water bath, and then the solution was stirred for 3 hr.

The obtained white precipitate was filtered by suction, and then the remaining methylenechloride was removed at 50° C. for 3 hr in vacuum oven to obtain 2-methyl-4-isothiazolin-3-one.HCl (28 g, 92.7 mol %).

$^1$H-NMR(100 MHz, $D_2O$):δ ppm; 8.54(d, 5H), 6.36(d, 4H), 3.42(s, $CH_3$)

EXAMPLE 5

A thermometer and dropping funnel were equiped with 1 l three-necked flask, and N,N dimethyl 3,3'-dithiodipropionamide (23.6 g, 0.1 mol) was dissolved in 350 ml of methylenechloride in the flask. The solution was maintained below −15° C. in cryostat, and herein sulfurylchloride (28.35 g, 0.21 mol) was added dropwise and simultaneously stirred for 3 hr.

After stirring at −5° C. for 1 hr, the temperature was slowly increased to room temperature and maintained at 40° C. in water bath, and then the solution was stirred for 3 hr.

The obtained white precipitate was filtered by suction, and then the remaining methylenechloride was removed at 50° C. for 3 hr in vacuum oven to obtain 2-methyl-4-isothiazolin-3-one.HCl (27.5 g, 90.7 mol %).

$^1$H-NMR(100 MHz, $D_2O$):δ ppm; 8.54(d, 5H), 6.33(d, 4H), 3.41(s, $CH_3$)

EXAMPLE 6

A thermometer and dropping funnel were equiped with 1 l three-necked flask, N,N dimethyl and 3,3'-dithiodipropionamide (23.6 g, 0.1 mol) was dissolved in 350 ml of methylenechloride in the flask. The solution was maintained below −15° C. in cryostat, and herein sulfurylchloride (27.0 g, 0.2 mol) was added dropwise and simultaneously stirred for 3 hr.

After stirring at −5° C. for 1 hr, the temperature was slowly increased to room temperature and maintained at 40° C. in water bath, and then the solution was stirred for 3 hr.

The obtained white precipitate was filtered by suction, and then the remaining methylenechloride was removed at 50° C. for 3 hr in vacuum oven to obtain 2-methyl-4-isothiazolin-3-one.HCl (27.9 g, 92 mol %).

$^1$H-NMR(100 MHz, $D_2O$):δ ppm: 8.56(d, 5H), 6.37(d, 4H), 3.41(s, $CH_3$)

EXAMPLE 7

A thermometer and dropping funnel were equiped with 1 l three-necked flask, N,N dimethyl and 3,3'-dithiodipropionamide (23.6 g, 0.1 mol) was dissolved in 350 ml of chloroform in the flask. The solution was maintained below −15° C. in cryostat, and herein sulfurylchloride (40.5 g, 0.3 mol) was added dropwise and simultaneously stirred for 3 hr.

After stirring at 0° C. for 1 hr, the temperature was slowly increased to room temperature and maintained at 25° C. in water bath, and then the solution was stirred for 3 hr.

The obtained white precipitate was filtered by suction, and then the remaining chloroform was removed at 50° C. for 3 hr in vacuum oven to obtain 2-methyl-4-isothiazolin-3-one.HCl (27.2 g, 89.7 mol %).

$^1$H-NMR(100 MHz, $D_2O$):δ ppm; 8.50(d, 5H), 6.32(d, 4H), 3.43(s, $CH_3$)

EXAMPLE 8

A thermometer and dropping funnel were equiped with 1 l three-necked flask, and 3,3'-dithiodipropionamide (23.6 g, 0.1 mol) was dissolved in 350 ml of chloroform in the flask. The solution was maintained below −10° C. in cryostat, and herein sulfurylchloride (33.7 g, 0.25 mol) was added dropwise and simultaneously stirred for 3 hr.

After stirring at 0° C. for 1 hr, the temperature was slowly increased to room temperature and maintained at 30° C. in water bath, and then the solution was stirred for 3 hr.

The obtained white precipitate was filtered by suction, and then the remaining chloroform was removed at 50° C. for 3 hr in vacuum oven to obtain 2-methyl-4-isothiazolin-3-one.HCl (27.5 g, 90.7 mol %).

$^1$H-NMR(100 MHz, $D_2O$):δ ppm; 8.51(d, 5H), 6.33(d, 4H), 3.40(s, $CH_3$)

EXAMPLE 9

A thermometer and dropping funnel were equiped with 1 l three-necked flask, N,N dimethyl and 3,3'-dithiodipropionamide (23.6 g, 0.1 mol) was dissolved in 350 ml of chloroform in the flask. The solution was maintained below −5° C. in cryostat, and herein sulfurylchloride (28.25 g, 0.21 mol) was added drop wise and simultaneously stirred for 3 hr.

After stirring at 0° C. for 1 hr, the temperature was slowly increased to room temperature and maintained at 35° C. in water bath, and then the solution was stirred for 3 hr.

The obtained white precipitate was filtered by suction, and then the remaining chloroform was removed at 50° C. for 3 hr in vacuum oven to obtain 2-methyl-4-isothiazolin-3-one.HCl (27.7 g, 91.3 mol %).

$^1$H-NMR(100 MHz, $D_2O$):δ ppm; 8.55(d, 5H), 6.32(d, 4H), 3.40(s, $CH_3$)

EXAMPLE 10

A thermometer and dropping funnel were equiped with 1 l three-necked flask, N,N dimethyl and 3,3'-dithiodipropionamide (23.6 g, 0.1 mol) was dissolved in 350 ml of chloroform in the flask. The solution was maintained below 5° C. in cryostat, and herein sulfurylchloride (27.0 g, 0.2 mol) was added dropwise and simultaneously stirred for 3 hr.

After stirring at 0° C. for 1 hr, the temperature was slowly increased to room temperature and maintained at 40° C. in water bath, and then the solution was stirred for 3 hr.

The obtained white precipitate was filtered by suction, and then the remaining chloroform was removed at 50° C. for 3 hr in vacuum oven to obtain 2-methyl-4-isothiazolin-3-one.HCl (28.0 g, 92.3 mol %).

$^1$H-NMR(100 MHz, $D_2O$):δ ppm; 8.47(d, 5H), 6.31(d, 4H), 3.42(s, $CH_3$)

EXAMPLE 11

A thermometer and dropping funnel were equiped with 1 l three-necked flask, and 3,3'-dithiodipropionamide (23.6 g, 0.1 mol) was dissolved in 350 ml of chloroform in the flask. The solution was maintained below −10° C. in cryostat, and herein sulfurylchloride (28.35 g, 0.21 mol) was added dropwise and simultaneously stirred for 3 hr.

After stirring at 0° C. for 1 hr, the temperature was slowly increased to room temperature and maintained at 40° C. in water bath, and then the solution was stirred for 3 hr.

The obtained white precipitate was filtered by suction, and then the remaining chloroform was removed at 50° C. for 3 hr in vacuum oven to obtain 2-methyl-4-isothiazolin-3-one.HCl (27.6 g, 91 mol %).

$^1$H-NMR(100 MHz, D$_2$O):δ ppm; 8.49(d, 5H), 6.33(d, 4H), 3.41(s, CH$_3$)

EXAMPLE 12

A thermometer and dropping funnel were equiped with 1 l three-necked flask, and 3,3'-dithiodipropionamide (23.6 g, 0.1 mol) was dissolved in 350 ml of chloroform in the flask. The solution was maintained below −15° C. in cryostat, and herein sulfurylchloride (27.0 g, 0.2 mol) was added dropwise and simultaneously stirred for 3 hr.

After stirring at −5° C. for 1 hr, the temperature was slowly increased to room temperature and maintained at 40° in water bath, and then the solution was stirred for 3 hr.

The obtained white precipitate was filtered by suction, and then the remaining chloroform was removed at 50° C. for 3 hr in vacuum oven to obtain 2-methyl-4-isothiazolin-3-one.HCl (28.0 g, 92.3 mol %).

$^1$H-NMR(100 MHz, D$_2$O):δ ppm; 8.52(d, 5H), 6.34(d, 4H), 3.42(s, CH$_3$)

EXAMPLE 13

A thermometer and dropping funnel were equiped with 1 l three-necked flask, N,N dimethyl and 3,3'-dithiodipropionamide (23.6 g, 0.1 mol) was dissolved in 350 ml of 1,1,1-trichloroethane in the flask. The solution was maintained below 0° C. in cryostat, and herein sulfurylchloride (40.5 g, 0.3 mol) was added dropwise and simultaneously stirred for 3 hr.

After stirring at 0° C. for 1 hr, the temperature was slowly increased to room temperature and maintained at 25° C. in water bath, and then the solution was stirred for 3 hr.

The obtained white precipitate was filtered by suction, and then the remaining 1,1,1-trichloroethane was removed at 50° C. for 3 hr in vacuum oven to obtain 2-methyl-4-isothiazolin-3-one.HCl (27.3 g, 90 mol %).

$^1$H-NMR(100 MHz, D$_2$O):δ ppm; 8.47(d, 5H), 6.34(d, 4H), 3.41(s, CH$_3$)

EXAMPLE 14

A thermometer and dropping funnel were equiped with 1 l three-necked flask, N,N dimethyl and 3,3'-dithiodipropionamide (23.6 g, 0.1 mol) was dissolved in 350 ml of 1,1,1-trichloroethane in the flask. The solution was maintained below 5° C. in cryostat, and herein sulfurylchloride (33.75 g, 0.25 mol) was added dropwise and simultaneously stirred for 3 hr.

After stirring at 0° C. for 1 hr, the temperature was slowly increased to room temperature and maintained at 30° in water bath, and then the solution was stirred for 3 hr.

The obtained white precipitate was filtered by suction, and then the remaining 1,1,1-trichloroethane was removed at 50° C. for 3 hr in vacuum oven to obtain 2-methyl-4-isothiazolin-3-one.HCl (27.5 g, 90.7 mol %).

$^1$H-NMR(100 MHz, D$_2$O):δ ppm; 8.50(d, 5H), 6.34(d, 4H), 3.43(s, CH$_3$)

EXAMPLE 15

A thermometer and dropping funnel were equiped with 1 l three-necked flask, N,N dimethyl and 3,3'-dithiodipropionamide (23.6 g, 0.1 mol) was dissolved in 350 ml of 1,1,1-trichloroethane in the flask. The solution was maintained below −5° C. in cryostat, and herein sulfurylchloride (28.35 g, 0.2 mol) was added dropwise and simultaneously stirred for 3 hr.

After stirring at 0° C. for 1 hr, the temperature was slowly increased to room temperature and maintained at 35° C. in water bath, and then the solution was stirred for 3 hr.

The obtained white precipitate was filtered by suction, and then the remaining 1,1,1-trichloroethane was removed at 50° C. for 3 hr in vacuum oven to obtain 2-methyl-4-isothiazolin-3-one.HCl (27.3 g, 90 mol %).

$^1$H-NMR (100 MHz, D$_2$O):δ ppm; 8.54(d, 5H), 6.34(d, 4H), 3.40(s, CH$_3$)

EXAMPLE 16

A thermometer and dropping funnel were equiped with 1 l three-necked flask, N,N, dimethyl and 3,3'-dithiodipropionamide (23.6 g, 0. 1 mol) was dissolved in 350 ml of 1,1,1-trichloroethane in the flask. The solution was maintained below −5° C. in cryostat, and heroin sulfurylchloride (27.0 g, 0.2 mol) was added dropwise and simultaneously stirred for 3 hr.

After stirring at 0° C. for 1 hr, the temperature was slowly increased to room temperature and maintained at 40° C. in water bath, and then the solution was stirred for 3 hr.

The obtained white precipitate was filtered by suction, and then the remaining 1,1,1-trichloroethane was removed at 50° C. for 3 hr in vacuum oven to obtain 2-methyl-4-isothiazolin-3-one.HCl (27.5 g, 90.7 mol %).

$^1$H-NMR(100 MHz, D$_2$O):δ ppm; 8.54(d, 5H), 6.33(d, 4H), 3.41(s, CH$_3$)

EXAMPLE 17

A thermometer and dropping funnel were equiped with 1 l three-necked flask, N,N dimethyl and 3,3'-dithiodipropionamide (23.6 g, 0.1 mol) was dissolved in 350 ml of 1,1,1-trichloroethane in the flask. The solution was maintained below −10° C. in cryostat, and herein sulfurylchloride (28.35 g, 0.21 mol) was added dropwise and simultaneously stirred for 3 hr.

After stirring at −5° C. for 1 hr, the temperature was slowly increased to room temperature and maintained at 40° C. in water bath, and then the solution was stirred for 3 hr.

The obtained white precipitate was filtered by suction, and then the remaining 1,1,1-trichloroethane was removed at 40° C. for 3 hr in vacuum oven to obtain 2-methyl-4-isothiazolin-3-one.HCl (27.8 g, 91.7 mol %).

$^1$H-NMR (100 MHz, D,O):δ ppm; 8.53(d, 5H), 6.34(d, 4H), 3.42(s, CH$_3$)

EXAMPLE 18

A thermometer and dropping funnel were equiped with 1 l three-necked flask, N,N, dimethyl and 3,3'-dithiodipropionamide (23.6 g, 0.1 mol) was dissolved in 350 ml of 1,1,1-trichloroethane in the flask. The solution was maintained below 5° in cryostat, and herein sulfurylchloride (27.0 g, 0.2 mol) was added dropwise and simultaneously stirred for 3 hr.

After stirring at −5° C. for 1 hr, the temperature was slowly increased to room temperature and maintained at 40° in water bath, and then the solution was stirred for 3 hr.

The obtained white precipitate was filtered by suction, and then the remaining 1,1,1-trichloroethane was removed at 50° C. for 3 hr in vacuum oven to obtain 2-methyl-4-isothiazolin-3-one.HCl (27.6 g, 91 mol %).

$^1$H-NMR(100 MHz, $D_2O$):δ ppm; 8.56(d, 5H), 6.37(d, 4H), 3.43(s, $CH_3$)

EXAMPLE 19

A thermometer and dropping funnel were equiped with 1 l three-necked flask, and N,N-di-n-octyl-3,3'-dithiodipropionamide (43.25 g, 0.1 mol) was dissolved in 350 ml of methylenechloride in the flask. The solution was maintained below 5° C. in cryostat, and herein sulfurylchloride (16.2 g, 0.12 mol) was added dropwise and simultaneously stirred for 3 hr.

After stirring at 0° C. for 1 hr, the temperature was slowly increased to room temperature and maintained at 25° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 2-n-octyl-4-isothiazolin-3-one.HCl (44.9 g, 90 mol %).

$^1$H-NMR(100 MHz, $CDCl_3$):δ ppm; 0.87(m), 1.27(s), 1.67(m), 3.72(t), 6.31(d), 8.11(d)

EXAMPLE 20

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained below 5° C. in cryostat, and herein sulfurylchloride (14.85 g, 0.11 mol) was added dropwise and simultaneously stirred for 3 hr.

After stirring at 0° C. for 1 hr, the temperature was slowly increased to room temperature and maintained at 30° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 2-n-octyl-4-isothiazolin-3-one.HCl (45.9 g, 92 mol %).

$^1$H-NMR(100 MHz, $CDCl_3$):δ ppm; 0.88(m), 1.27(s), 1.69(m), 3.74(t), 7.16(d), 8.93(d)

EXAMPLE 21

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained below −5° C. in cryostat, and herein sulfurylchloride (13.5 g, 0.1 mol) was added dropwise and simultaneously stirred for 3 hr.

After stirring at −5° C. for 1 hr, the temperature was slowly increased to room temperature and maintained at 35° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 2-n-octyl-4-isothiazolin-3-one.HCl (44.91 g, 90 mol %).

$^1$H-NMR(100 MHz, $CDCl_3$):δ ppm; 0.87(m), 1.26(s), 1.74(m), 3.75(t), 6.90(d), 8.79(d)

EXAMPLE 22

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained below −5° C. in cryostat, and herein sulfurylchloride (17.55 g, 0.13 mol) was added dropwise and simultaneously stirred for 3 hr.

After stirring at 0° C. for 1 hr, the temperature was slowly increased to room temperature and maintained at 4° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 2-n-octyl-4-isothiazolin-3-one.HCl (46.1 g, 92.5 mol %).

$^1$H-NMR(100 MHz, $CDCl_3$):δ ppm; 0.87(m), 1.26(s), 1.67(m), 3.73(t), 6.25(d), 8.05(d)

EXAMPLE 23

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained below −15° C. in cryostat, and herein sulfurylchloride (18.9 g, 0.14 mol) was added dropwise and simultaneously stirred for 3 hr.

After stirring at −5° C. for 1 hr, the temperature was slowly increased to room temperature and maintained at 40° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 2-n-octyl-4-isothiazolin-3-one- . HCl (46.4 g, 93 mol %).

$^1$H-NMR(100 MHz, CDCl$_3$):δ ppm; 0.87(m), 1.27(s), 1.67(m), 3.76(t) 6.23(d), 8.02(d)

EXAMPLE 24

A thermometer and dropping funnel were equiped with 1 l three-necked flask, and N,N'-di-n-octyl-3,3'-dithiodipropionamide (43.25 g, 0.1 mol) was dissolved in 350 ml of chloroform in the flask. The solution was maintained below 5° C. in cryostat, and herein sulfurylchloride (13.5 g, 0.1 mol) was added dropwise and simultaneously stirred for 3 hr.

After stirring at 0° C. for 1 hr, the temperature was slowly increased to room temperature and maintained at 25° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove chloroform and to obtain 2-n-octyl-4-isothiazolin-3-one.HCl (45.4 g, 91 mol %).

$^1$H-NMR(100 MHz, CDCl$_3$):δ ppm: 0.88(m), 1.28(s), 1.58(m), 4.02(t) 6.79(d), 8.75(d)

EXAMPLE 25

A thermometer and dropping funnel were equiped with 1 l three-necked flask, and N,N'-di-n-octyl-3,3'-dithiodipropionamide (43.25 g, 0.1 mol) was dissolved in 350 ml of chloroform in the flask. The solution was maintained below 5° C. in cryostat, and herein sulfurylchloride (14.85 g, 0.1 mol) was added dropwise and simultaneously stirred for 3 hr.

After stirring at 0° C. for 1 hr, the temperature was slowly increased to room temperature and maintained at 30° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove chloroform and to obtain 2-n-octyl-4-isothiazolin-3-one.HCl (45.63 g, 91.5 mol %).

$^1$H-NMR(100 MHz, CDCl$_3$):δ ppm; 0.87(m), 1.27(s), 1.55(m), 3.93(t) 6.70(d), 8.48(d)

EXAMPLE 26

A thermometer and dropping funnel were equiped with 1 l three-necked flask, and N,N'-di-n-octyl-3,3'-dithiodipropionamide (43.25 g, 0.1 mol) was dissolved in 350 ml of chloroform in the flask. The solution was maintained below −5° C. in cryostat, and herein sulfurylchloride (16.2 g, 0.12 mol)was added dropwise and simultaneously stirred for 3 hr.

After stirring at −5° C. for 1 hr, the temperature was slowly increased to room temperature and maintained at 35° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove chloroform and to obtain 2-n-octyl-4-isothiazolin-3-one.HCl (44.91 g, 90 mol %).

$^1$H-NMR(100 MHz, CDCl$_3$)δ ppm; 0.88(m), 1.27(s), 1.64(m), 3.81(t) 6.31(d), 8.11 (d)

EXAMPLE 27

A thermometer and dropping funnel were equiped with 1 l three-necked flask, and N,N'-di-n-octyl-3,3'-dithiodipropionamide (43.25 g, 0.1 mol) was dissolved in 350 ml of chloroform in the flask. The solution was maintained below −5° C. in cryostat, and herein sulfurylchloride (17.55 g, 0.13 mol) was added dropwise and simultaneously stirred for 3 hr.

After stirring at 0° C. for 1 hr, the temperature was slowly increased to room temperature and maintained at 40° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove chloroform and to obtain 2-n-octyl-4-isothiazolin-3-one.HCl (45.13 g, 90.5 mol %).

$^1$H-NMR(100 MHz, CDCl$_3$):δ ppm; 0.88(m), 1.26(s), 1.69(m), 4.06(t), 7.15(d), 8.92(d)

EXAMPLE 28

A thermometer and dropping funnel were equiped with 1 l three-necked flask, and N,N'-di-n-octyl-3,3'-dithiodipropionamide (43.25 g, 0.1 mol) was dissolved in 350 ml of chloroform in the flask. The solution was maintained below −15° C. in cryostat, and here in sulfurylchloride ( 18.9 g, 0.14 mol) was added dropwise and simultaneously stirred for 3 hr.

After stirring at −5° C. for 1 hr, the temperature was slowly increased to room temperature and maintained at 40° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove chloroform and to obtain 2-n-octyl-4-isothiazolin-3-one.HCl (45.88 g, 92 mol %).

$^1$H-NMR(100 MHz, CDCl$_3$)δ ppm; 0.87(m), 1.26(s), 1.66(m), 3.78(t), 6.23(d), 8.06(d)

EXAMPLE 29

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained below 5° C. in cryostat, and herein sulfurylchloride (270 g, 2.0 mol) was added dropwise and simultaneously stirred for 3 hr.

After stirring at 0° C. for 1 hr, the temperature was slowly increased to room temperature and maintained at 25° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 4,5-dichloro 2-n-octyl-4-isothiazolin-3-one-.HCl (57.4 g, 90 mol %).

$^{H-NMR}$(100 MHz, CDCl$_3$)δ ppm; 0.88(m), 1.27(s), 1.69(m), 3.79(t)

EXAMPLE 30

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained below 5° C. in cryostat, and herein sulfurylchloride (267.3 g, 1.98 mol) was added dropwise and simultaneously stirred for 5 hr.

After stirring at 0° C. for 1 hr, the temperature was slowly increased to room temperature and maintained at 30° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 4,5-dichloro 2-n-octyl-4-isothiazolin-3-one-.HCl (57.7 g, 90.5 mol %).

$^1$H-NMR(100 MHz, CDCl$_3$):δ ppm; 0.88(m), 1.27(s), 1.69(m), 3.79(t)

EXAMPLE 31

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained below −5° C. in cryostat, and herein sulfurylchloride (264.6 g, 1.96 mol) was added dropwise and simultaneously stirred for 5 hr.

After stirring at −5° C. for 1 hr, the temperature was slowly increased to room temperature and maintained at 35° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 4,5-dichloro 2-n-octyl-4-isothiazolin-3-one-.HCl (58 g, 91 mol %).

$^1$H-NMR(100 MHz, CDCl$_3$):δ ppm; 0.88(m), 1.27(s), 1.68(m), 3.79(t)

EXAMPLE 32

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained below −5° C. in cryostat, and herein sulfurylchloride (26 1.9 g, 1.94 mol) was added dropwise and simultaneously stirred for 5 hr.

After stirring at 0° C. for 1 hr, the temperature was slowly increased to room temperature and maintained at 40° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 4,5-dichloro 2-n-octyl-4-isothiazolin-3-one-.HCl (57.6 g, 90.5 mol %).

$^1$H-NMR(100 MHz, CDCl$_3$)δ ppm; 0.88(m), 1.27(s), 1.69(m), 3.80(t)

EXAMPLE 33

A thermometer and dropping funnel were equiped with 1 l three-necked flask, and N,N'-di-n-octyl-3,3'-dithiodipropionamide (43.25 g, 0.1 mol)was dissolved in 350 ml of methylenechloride in the flask. The solution was maintained below −15° C. in cryostat, and herein sulfurylchloride (259.2 g, 1.92 mol) was added dropwise and simultaneously stirred for 5 hr.

After stirring at −5° C. for 1 hr, the temperature was slowly increased to room temperature and maintained at 40° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove methylenechloride and to obtain 4,5-dichloro 2-n-octyl-4-isothiazolin-3-one-.HCl (58.6 g, 92 mol %).

$^1$H-NMR(100 MHz, CDCl$_3$)δ ppm; 0.88(m), 1.26(s), 1.68(m), 3.79(t)

EXAMPLE 34

A thermometer and dropping funnel were equiped with 1 l three-necked flask, and N,N'-di-n-octyl-3,3'-dithiodipropionamide (43.25 g, 0.1 mol) was dissolved in 350 ml of chloroform in the flask. The solution was maintained below 5° C. in cryostat, and herein sulfurylchloride (256.5 g, 1.9 mol) was added dropwise and simultaneously stirred for 5 hr.

After stirring at 0° C. for 1 hr, the temperature was slowly increased to room temperature and maintained at 25° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove chloroform and to obtain 2-n-octyl-4-isothiazolin-3-one.HCl (58.1 g, 91 mol %).

$^1$H-NMR(100 MHz, CDCl$_3$) δ ppm; 0.88(m), 1.27(s), 1.68(m), 3.80(t)

EXAMPLE 35

A thermometer and dropping funnel were equiped with 1 l three-necked flask, and N,N'-di-n-octyl-3,3'-dithiodipropionamide (43.25 g, 0.1 mol) was dissolved in 350 ml of chloroform in the flask. The solution was maintained below 5° C. in cryostat, and herein sulfurylchloride (260.55 g, 1.93 mol) was added dropwise and simultaneously stirred for 5 hr.

After stirring at 0° C. for 1 hr, the temperature was slowly increased to room temperature and maintained at 30° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove chloroform and to obtain 4,5-dichloro 2-n-octyl-4-isothiazolin-3-one.HCl (58.4 g, 91.5 mol %).

$^1$H-NMR(100 MHz, CDCl$_3$):δ ppm; 0.87(m), 1.27(s), 1.68(m), 3.79(t)

EXAMPLE 36

A thermometer and dropping funnel were equiped with 1 l three-necked flask, and N,N'-di-n-octyl-3,3'-dithiodipropionamide (43.25 g, 0.1 mol) was dissolved in 350 ml of ethylacetate in the flask. The solution was maintained below 5° C. in cryostat, and herein sulfurylchloride (81 g, 0.6 mol) was added dropwise and simultaneously stirred for 5 hr.

After stirring at 0° C. for 1 hr, the temperature was slowly increased to room temperature and maintained at 25° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove ethylacetate and to obtain 4,5-dichloro 2-n-octyl-4-isothiazolin-3-one.HCl (57.4 g, 90 mol %).

$^1$H-NMR(100 MHz, CDCl$_3$):δ ppm; 0.87(m), 1.27(s), 1.68(m), 3.78(t)

EXAMPLE 37

A thermometer and dropping funnel were equiped with 1 l three-necked flask, and N,N'-di-n-octyl-3,3'-dithiodipropionamide (43.25 g, 0.1 mol) was dissolved in 350 ml of ethylacetate in the flask. The solution was maintained below 5° in cryostat, and herein sulfurylchloride (87.75 g, 0.65 mol) was added dropwise and simultaneously stirred for 5 hr.

After stirring at 0° C. for 1 hr, the temperature was slowly increased to room temperature and maintained at 30° C. in water bath, and then the solution was stirred for 3 hr to obtain yellow solution.

After reacting tinder the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove ethylacetate and to obtain 4,5-dichloro 2-n-octyl-4-isothiazolin-3-one.HCl (57.7 g, 90.5 mol %).

$^1$H-NMR(100 MHz, CDCl$_3$):δ ppm; 0.88(m), 1.26(s), 1.67(m), 3.79(t)

EXAMPLE 38

A thermometer and dropping funnel were equiped with 1 l three-necked flask, and N,N'-di-n-octyl-3,3'-dithiodipropionamide (43.25 g, 0.1 mol) was dissolved in 350 ml of ethylacetate in the flask. The solution was maintained below −5° C. in cryostat, and herein sulfurylchloride (94.5 g, 0.7 mol) was added dropwise and simultaneously stirred for 5 hr.

After stirring at −5° C. for 1 hr, the temperature was slowly increased to room temperature and maintained at 35° C. in water bath, and then the solution was stirred for 3 hr to obtain yellow solution.

After reacting under the above temperature, 100 ml of pure water was poured in the obtained yellow solution to be separated by separatory funnel, and then the obtained organic solvent layers were reacted with 30 g of anhydride magnesium sulfate to dehydrate in the organic solvent layers.

The solvent in the organic solvent layers was removed in rotary evaporator, and then the residue was maintained at 50° C. for 3 hr in vacuum oven to remove ethylacetate and to obtain 4,5-dichloro 2-n-octyl-4-isothiazolin-3-one.HCl (58 g, 91 mol %).

$^1$H-NMR(100 MHz. CDCl$_3$):δ ppm; 0.88(m), 1.27(s), 1.67(m), 3.79(t)

COMPARATIVE EXAMPLE 1

A thermometer and dropping funnel were equiped with 1 l three-necked flask, and 3,3'-dithiodipropionamide (23.6 g, 0.1 mol) was dissolved in 350 ml of methylenechloride in the flask. The solution was maintained over 70° in water bath, and herein sulfurylchloride (40.5 g, 0.3 mol) was added dropwise and simultaneously stirred for 3 hr.

Then, since methylenechloride vapor was occured, the reaction could not be carried out.

COMPARATIVE EXAMPLE 2

A thermometer and dropping funnel were equiped with 1 l three-necked flask, and 3,3'-dithiodipropionamide (23.6 g, 0.1 mol) was dissolved in 350 ml of chloroform in the flask. The solution was maintained over 70° C. in water bath, and herein sulfurylchloride (40.5 g, 0.3 mol) was added dropwise and simultaneously stirred for 3 hr.

Then, since chloroform vapor was occured, the reaction could not be carried out.

COMPARATIVE EXAMPLE 3

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask. The solution was maintained over 70° C. in water bath, and herein sulfurylchloride (40.5 g, 0.3 mol) was added dropwise and simultaneously stirred for 3 hr.

Then, since methylenechloride vapor was occured, the reaction could not be carried out.

COMPARATIVE EXAMPLE 4

A thermometer and dropping funnel were equiped with 1 l three-necked flask, and N,N'-di-n-octyl-3,3'-dithiodipropionamide (43.25 g, 0.1 mol) was dissolved in 350 ml of chloroform in the flask. The solution was maintained over 70° C. in water bath, and herein sulfurylchloride (40.5 g, 0.3 mol) was added dropwise and simultaneously stirred for 3 hr.

Then, since chloroform vapor was occured, the reaction could not be carried out.

COMPARATIVE EXAMPLE 5

A thermometer and dropping funnel were equiped with 1 l three-necked flask, and N,N'-di-n-octyl-3,3'-dithiodipropionamide (43.25 g, 0.1 mol) was dissolved in 350 ml of methylenechloride in the flask.

The solution was maintained below 5° C. in cryostat, and herein sulfurylchloride (12.15 g, 0.09 mol) was added dropwise and simultaneously stirred for 3 hr.

After stirring at 0° C. for 1 hr, the temperature was increased to room temperature and maintained at 25° C. in water bath, and then the solution was stirred for 3 hr.

As the result of reaction, the desired compound was not prepared because of the present of plenty of unreacted compounds.

What is claimed is:

1. A process for selectively preparing a 4-isothiazolin-3-one derivative of formula (I) comprising the steps of preparing 3,3'-dithio propionyldichloride of formula (II) by reacting 3,3'-dithiodipropionic acid with thionylchloride, reacting said 3,3'-dithio propionyldichloride with an amine compound to prepare a 3,3'-dithio propionamide derivative of formula (III), and cyclizing said 3,3'-dithio propionamide derivative by adding sulfuryl chloride, wherein the molar proportion of said 3,3'-dithio propionamide derivative to said sulfuryl chloride is between 1:1 and 1:3 and said cyclizing step is carried out in an organic solvent at a temperature of between −20 and 5 degrees C.,

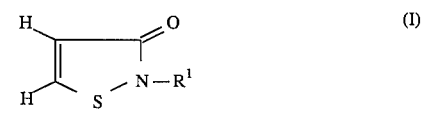

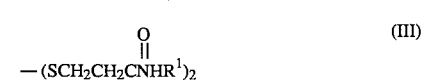

wherein R$^1$ is methyl or n-octyl.

2. The process of claim 1, wherein said organic solvent is selected from the group consisting of methylene chloride, chloroform and 1,1,1-trichloroethane.

3. A process for selectively preparing a 4-isothiazolin-3-one derivative of formula (I) comprising the steps of preparing 3,3'-dithio propionyldichloride of formula (II) by reacting 3,3'-dithiodipropionic acid with thionylchloride, reacting said 3,3'-dithio propionyldichloride with an amine compound to prepare a 3,3'-dithio propionamide derivative of formula (III), and cyclizing said 3,3'-dithio propionamide derivative by adding sulfuryl chloride, wherein the molar proportion of said 3,3'-dithio propionamide derivative to said sulfuryl chloride is between 1:6 and 1:25 and said cyclizing step is carried out in an organic solvent at a temperature of between −20 and 5 degrees C.,
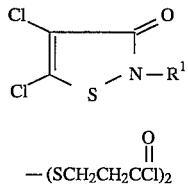  (I)
—(SCH₂CH₂CCl)₂  (II)
  (III)
wherein $R^1$ is methyl or n-octyl.
4. The process of claim 3, wherein said organic solvent is selected from the group consisting of methylene chloride, chloroform and 1,1,1-trichloroethane.
* * * * *

UNITED STATES PATENT AND TRADEMARK OFFICE
CERTIFICATE OF CORRECTION

PATENT NO. : 5,453,507

DATED : February 9, 1999

INVENTOR(S) : Hahn, et al

It is certified that error appears in the above-identified patent and that said Letters Patent is hereby corrected as shown below:

On the title page, item [75] inventors should read:

-- Soon Jong Hahn, Seoul; Jin Man Kim; Young Park, both of Kyungki, all of Rep. of Korea --

Signed and Sealed this

Thirteenth Day of July, 1999

Attest:

Q. TODD DICKINSON

*Attesting Officer*  *Acting Commissioner of Patents and Trademarks*